United States Patent
Alonzo et al.

(10) Patent No.: US 11,975,008 B2
(45) Date of Patent: May 7, 2024

(54) PHARMACEUTICAL COMPOSITIONS COMPRISING A JAK INHIBITOR

(71) Applicant: Galapagos NV, Mechelen (BE)

(72) Inventors: David Alonzo, Foster City, CA (US); Bei Li, Foster City, CA (US); Dimitrios Stefanidis, Saratoga, CA (US)

(73) Assignee: GALAPAGOS NV, Mechelen (BE)

( * ) Notice: Subject to any disclaimer, the term of this patent is extended or adjusted under 35 U.S.C. 154(b) by 632 days.

(21) Appl. No.: 17/186,446

(22) Filed: Feb. 26, 2021

(65) Prior Publication Data

US 2021/0353634 A1 Nov. 18, 2021

Related U.S. Application Data

(63) Continuation of application No. 16/930,803, filed on Jul. 16, 2020, now abandoned, which is a continuation of application No. 15/918,765, filed on Mar. 12, 2018, now abandoned.

(60) Provisional application No. 62/536,614, filed on Jul. 25, 2017, provisional application No. 62/471,171, filed on Mar. 14, 2017.

(51) Int. Cl.
| | | |
|---|---|---|
| A61K 31/541 | (2006.01) | |
| A61K 9/20 | (2006.01) | |
| A61K 47/12 | (2006.01) | |
| A61P 29/00 | (2006.01) | |

(52) U.S. Cl.
CPC .............. *A61K 31/541* (2013.01); *A61K 9/20* (2013.01); *A61K 9/2009* (2013.01); *A61K 9/2013* (2013.01); *A61K 9/2018* (2013.01); *A61K 9/2054* (2013.01); *A61K 9/2059* (2013.01); *A61K 47/12* (2013.01); *A61P 29/00* (2018.01)

(58) Field of Classification Search
CPC ...... A61K 31/541; A61K 9/20; A61K 9/2009; A61K 9/2013; A61K 9/2018; A61K 9/2054; A61K 9/2059; A61K 47/12; A61P 29/00; A61P 1/00; A61P 19/02
See application file for complete search history.

(56) References Cited

FOREIGN PATENT DOCUMENTS

WO  WO 2015/117980 A1 * 8/2015 .......... A61K 31/541

* cited by examiner

*Primary Examiner* — Valerie Rodriguez-Garcia
*Assistant Examiner* — David M Shim
(74) *Attorney, Agent, or Firm* — ArentFox Schiff LLP (57) ABSTRACT

Pharmaceutical compositions comprising filgotinib maleate Form I characterized by an XRPD pattern substantially the same as shown in FIG. 1 and uses thereof are described herein.

12 Claims, 3 Drawing Sheets

PHARMACEUTICAL COMPOSITIONS COMPRISING A JAK INHIBITOR

CROSS-REFERENCE TO RELATED APPLICATIONS

This application claims the benefit of U.S. Provisional Application Ser. No. 62/471,171, filed Mar. 14, 2017, and U.S. Provisional Application Ser. No. 62/536,614, filed Jul. 25, 2017. The entireties of these applications are incorporated herein by reference.

BACKGROUND

Janus kinase (JAK) is a family of intracellular, nonreceptor tyrosine kinases that transduce cytokine-mediated signals via the JAK-STAT pathway. Filgotinib is a JAK1 selective inhibitor.

SUMMARY

Figure 1:
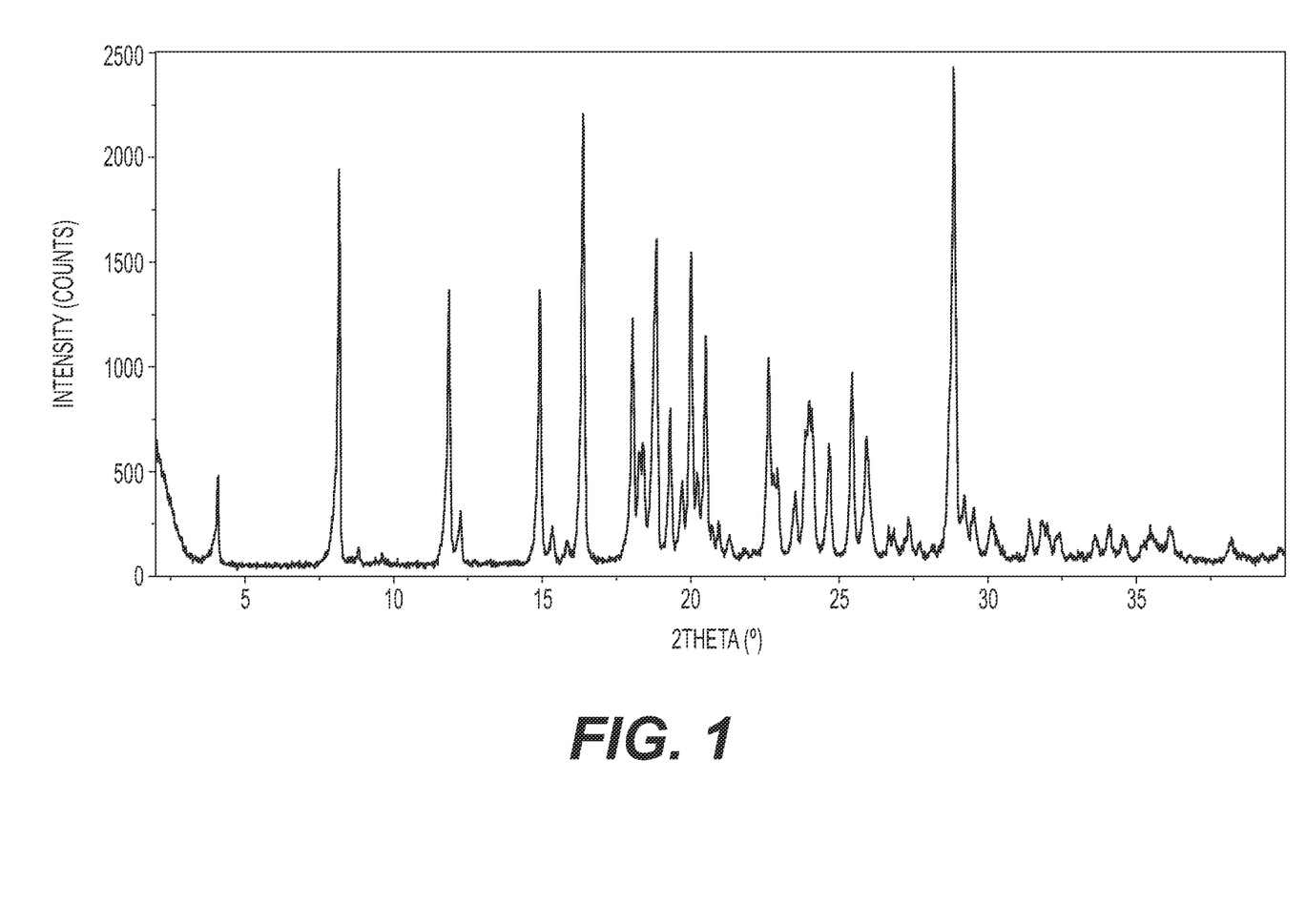
FIG. 1 is an X-ray powder diffraction (XRPD) pattern of filgotinib maleate Form I.
Figure 2:
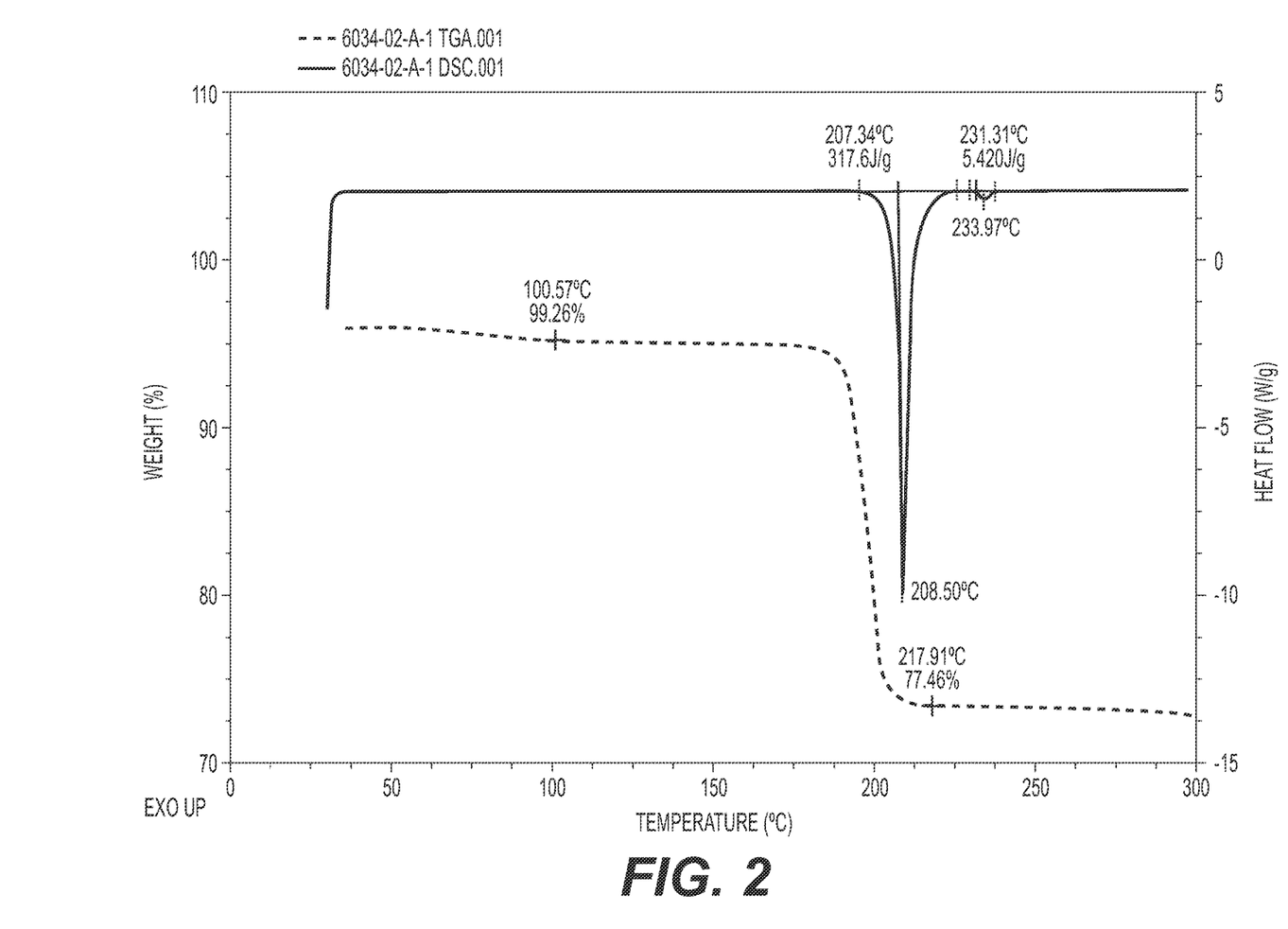
FIG. 2 is differential scanning calorimetry (DSC) curve and thermogravimetric analysis (TGA) of filgotinib maleate Form I.
Figure 3:
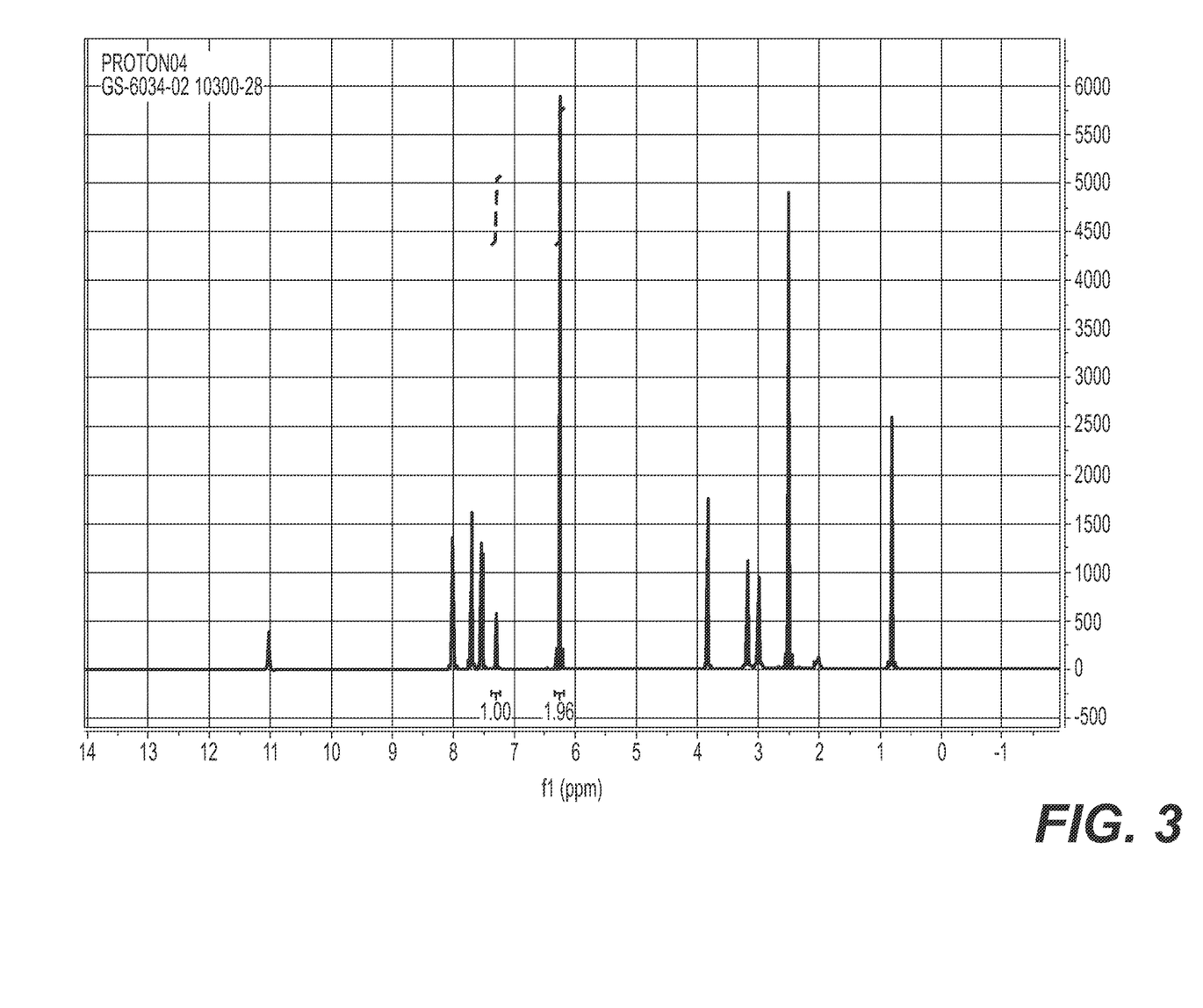
FIG. 3 is a proton nuclear magnetic resonance ($^1$H NMR) spectrum of filgotinib maleate Form I.

The present disclosure provides pharmaceutical compositions comprising a therapeutically effective amount of filgotinib maleate Form I. In some embodiments the filgotinib maleate Form I is characterized by an XRPD pattern comprising peaks at 8.2, 11.9, 16.4, and 18.9°2θ±0.2°2θ as determined on a diffractometer using Cu-Kα radiation. In some embodiments the filgotinib maleate Form I is characterized by an XRPD pattern substantially the same as shown in FIG. 1. In some embodiments the filgotinib maleate Form I is characterized by a differential scanning calorimetry (DSC) curve substantially the same as shown in FIG. 2. In some embodiments the filgotinib maleate Form I is characterized by thermogravimetric analysis (TGA) comprising a thermogram substantially the same as shown in FIG. 2. In some embodiments the filgotinib maleate Form I is characterized by a proton nuclear magnetic resonance spectrum ($^1$H NMR) substantially the same as shown in FIG. 3.

In some embodiments, a pharmaceutical composition disclosed herein further comprises fumaric acid. In some embodiments, a pharmaceutical composition disclosed herein further comprises magnesium stearate. In some embodiments, a pharmaceutical composition disclosed herein further comprises fumaric acid and magnesium stearate. In some embodiments, a pharmaceutical composition disclosed herein further comprises fumaric acid, magnesium stearate, microcrystalline cellulose, lactose monohydrate, pregelatinized starch, and colloidal silicon dioxide. In some embodiments, a pharmaceutical composition disclosed herein further comprises fumaric acid, magnesium stearate, microcrystalline cellulose, lactose monohydrate, pregelatinized starch, colloidal silicon dioxide, PEG 3350, polyvinyl alcohol, talc, titanium dioxide, and iron oxide red. In some embodiments, a pharmaceutical composition disclosed herein is in the form of a tablet.

In some embodiments a pharmaceutical composition disclosed herein is administered to a patient in need thereof to treat a disease or disorder mediated by JAK. In some embodiments a pharmaceutical composition disclosed herein is administered to a patient in need thereof to treat an inflammatory disease or disorder. In some embodiments a pharmaceutical composition disclosed herein is administered to a patient in need thereof to treat a disease or disorder selected from the group consisting of rheumatoid arthritis, Crohn's disease, ulcerative colitis, alopecia areata, uveitis, acute graft-versus-host disease, cutaneous lupus nephritis, membranous lupus nephritis, atopic dermatitis, psoriasis, ankylosing spondylitis, and psoriatic arthritis.

DETAILED DESCRIPTION

Filgotinib has the chemical name N-(5-(4-((1,1-dioxidothiomorpholino)methyl)phenyl)-[1,2,4]triazolo[1,5-a]pyridin-2-yl)cyclopropanecarboxamide and the following structure:

Filgotinib and methods of its preparation and therapeutic use are described in U.S. Pat. No. 8,563,545. Pharmaceutical compositions comprising filgotinib are described in International Application Publication No. WO 2015/117980. In particular, International Application Publication No. WO 2015/117980 describes formulations comprising a hydrochloric acid, and more particularly a hydrochloride trihydrate, of filgotinib. International Application Publication No. WO 2015/117980 states that stability problems were encountered when magnesium stearate was used as a lubricating agent in pharmaceutical compositions comprising the filgotinib salt, or a solvate or hydrate thereof.

Filgotinib Maleate Form I

The present disclosure provides pharmaceutical compositions comprising a therapeutically effective amount of filgotinib maleate Form I. In some embodiments filgotinib maleate Form I is characterized by an XRPD pattern comprising peaks at 8.2, 11.9, 16.4, and 18.9°2θ±0.2°2θ as determined on a diffractometer using Cu-Kα radiation. In some embodiments filgotinib maleate Form I is characterized by an XRPD pattern comprising one or more peaks selected from the group consisting of 28.9, 16.4, 8.2, 18.9, 20.0, 11.9, 14.9, 18.1, 20.5, and 22.6°2θ±0.2°2θ as determined on a diffractometer using Cu-Kα radiation. In some embodiments filgotinib maleate Form I is characterized by an XRPD pattern comprising one, two, three, four, five, six, or more peaks selected from the group consisting of 28.9, 16.4, 8.2, 18.9, 20.0, 11.9, 14.9, 18.1, 20.5, and 22.6°2θ±0.2°2θ as determined on a diffractometer using Cu-Kα radiation. In some embodiments filgotinib maleate Form I is characterized by an XRPD pattern comprising at least four peaks selected from the group consisting of 28.9, 16.4, 8.2, 18.9, 20.0, 11.9, 14.9, 18.1, 20.5, and 22.6°2θ±0.2°2θ as determined on a diffractometer using Cu-Kα radiation. In some embodiments filgotinib maleate Form I is characterized by an XRPD pattern comprising at least five peaks selected from the group consisting of 28.9, 16.4, 8.2, 18.9, 20.0, 11.9, 14.9, 18.1, 20.5, and 22.6°2θ±0.2°2θ as determined on a diffractometer using Cu-Kα radiation. In some embodiments filgotinib maleate Form I is characterized by an XRPD pattern comprising peaks at 28.9, 16.4, 8.2, 18.9, 20.0, 11.9, 14.9, 18.1, 20.5, and 22.6°2θ±0.2°2θ as determined on a diffractometer using Cu-Kα radiation. In some embodiments filgotinib maleate Form I is characterized by an XRPD pattern substantially the same as shown in FIG. 1. In some embodiments filgotinib maleate Form I is characterized by a differential scanning calorimetry (DSC) curve substantially the same as shown in FIG. 2. In some embodiments filgotinib maleate Form I is characterized by thermogravimetric analysis (TGA) comprising a thermogram substantially the same as shown in FIG. 2. In some embodiments filgotinib maleate Form I is characterized by a proton nuclear magnetic resonance spectrum ($^1$H NMR) substantially the same as shown in FIG. 3.

Definitions

As used in the present specification, the following words and phrases are generally intended to have the meanings as set forth below, except to the extent that the context in which they are used indicates otherwise.

The term "about" refers to a range of ±10%, unless otherwise specified.

The term "substantially the same as" when referring to, for example, an XRPD pattern, a DSC thermogram, or a TGA graph includes a pattern, thermogram or graph that is not necessarily identical to those depicted herein, but that falls within the limits of experimental error or deviations when considered by one of ordinary skill in the art.

The term "therapeutically effective amount" refers to an amount that is sufficient to effect treatment, as defined below, when administered to a mammal, e.g. a human, in need of such treatment. The therapeutically effective amount will vary depending upon the subject being treated, the weight and age of the subject, the severity of the disease condition, the manner of administration and the like, which can readily be determined by one of ordinary skill in the art.

As used herein, "treatment" or "treating" is an approach for obtaining beneficial or desired results. For purposes of the present disclosure, beneficial or desired results include, but are not limited to, alleviation of a symptom and/or diminishment of the extent of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder.

As used herein the term "inflammatory disease(s)" or "inflammatory disorder(s)" refers to a group of conditions that are characterized by excessive or abnormal inflammation. Symptoms of "inflammatory diseases" or "inflammatory disorders" may include chronic pain, redness, swelling, stiffness, and damage to normal tissues. Non-limiting examples of "inflammatory diseases" or "inflammatory disorders" include rheumatoid arthritis, Crohn's disease, ulcerative colitis, alopecia areata, uveitis, acute graft-versus-host disease, cutaneous lupus nephritis, membranous lupus nephritis, atopic dermatitis, psoriasis, ankylosing spondylitis, and psoriatic arthritis.

Pharmaceutical Compositions

The pharmaceutical compositions described herein are generally for oral administration. Pharmaceutical compositions intended for oral administration may further comprise sweetening agents, flavoring agents, coloring agents, coating agents, and/or preserving agents in order to provide a palatable preparation. In one embodiment, the pharmaceutical compositions are in the form of a tablet. Tablets may be prepared by compression or molding. Compressed tablets may be prepared by compressing in a suitable machine the active ingredient in a free-flowing form such as, for example, a powder or granules, optionally mixed with a binder, lubricant, inert diluent, or preservative. Molded tablets may be made by molding in a suitable machine a mixture of the powdered active ingredient moistened with an inert liquid diluent. The tablets may optionally be coated or scored.

The amount of active ingredient that is combined with the carrier material to produce a single dosage form will vary depending upon the patient treated. In some embodiments, pharmaceutical compositions described herein comprise about 127.24 mg of filgotinib maleate Form I. In some embodiments, pharmaceutical compositions described herein comprise about 127.2 mg of filgotinib maleate Form I. In some embodiments, pharmaceutical compositions described herein comprise about 127 mg of filgotinib maleate Form I. In some embodiments, pharmaceutical compositions described herein comprise about 254.48 mg of filgotinib maleate Form I. In some embodiments, pharmaceutical compositions described herein comprise about 254.5 mg of filgotinib maleate Form I. In some embodiments, pharmaceutical compositions described herein comprise about 254 mg of filgotinib maleate Form I.

Methods of Use

The pharmaceutical compositions disclosed herein may be administered in therapeutic methods to treat diseases or disorders that are mediated by JAK. In some embodiments the pharmaceutical compositions disclosed herein are administered to a patient in need thereof to treat an inflammatory disease or disorder. In some embodiments the pharmaceutical compositions disclosed herein are administered to a patient in need thereof to treat a disease or disorder selected from the group consisting of rheumatoid arthritis, Crohn's disease, ulcerative colitis, alopecia areata, uveitis, acute graft-versus-host disease, cutaneous lupus nephritis, membranous lupus nephritis, atopic dermatitis, psoriasis, ankylosing spondylitis, and psoriatic arthritis.

Combination Therapy

The pharmaceutical compositions disclosed herein may be administered in therapeutic methods in combination with one or more additional therapeutic agents that are effective to treat diseases or disorders mediated by JAK. In some embodiments the pharmaceutical compositions disclosed herein are administered to a patient in need thereof in combination with one or more additional therapeutic agents that are effective to treat an inflammatory disease or disorder. In some embodiments the pharmaceutical compositions disclosed herein are administered to a patient in need thereof in combination with one or more additional therapeutic agents that are effective to treat a disease or disorder selected from the group consisting of rheumatoid arthritis, Crohn's disease, ulcerative colitis, alopecia areata, uveitis, acute graft-versus-host disease, cutaneous lupus nephritis, membranous lupus nephritis, atopic dermatitis, psoriasis, ankylosing spondylitis, and psoriatic arthritis.

EXAMPLES

Example 1

Preparation and Characterization of N-(5-(4(1,1-dioxidothiomorpholino)methyl)phenyl)-[1,2,4]triazolo[1,5-a]pyridin-2-yl)cyclopropanecarboxamide maleate (Filgotinib Maleate) Form I Filgotinib maleate Form I was prepared by heating N-(5-(4-((1,1-dioxidothiomorpholino)methyl)phenyl)-[1,2,4]triazolo[1,5-a]pyridin-2-yl)cyclopropanecarboxamide with 2.1 mol. eq. of maleic acid in acetone/water (95:5 v/v) at about 50° C. for about 16 hours. Afterwards, the reaction contents were cooled to about 20° C. over about 1.5 hours and held at about 20° C. for about 2 hours. Next, the reaction contents were filtered. The wet cake was washed with acetone and dried under vacuum at about 50° C. with agitation.

Filgotinib maleate Form I was also be produced by mixing N-(5-(4-((1,1-dioxidothiomorpholino)methyl)phenyl)-[1,2,4]triazolo[1,5-a]pyridin-2-yl)cyclopropanecarboxamide with 2.1 mol. eq. maleic acid in acetonitrile/water (3:1 vol.) at about 55° C. Next, a small amount of N-(5-(4-((1,1-dioxidothiomorpholino)methyl)phenyl)-[1,2,4]triazolo[1,5-a]pyridin-2-yl)cyclopropanecarboxamide maleate Form I was added as seed. The reaction contents were held at the same temperature for about 4 hours. Afterwards, the reactor contents were cooled to about 0-about 5° C. at about 0.1° C./min and held overnight. The solids were then filtered and stored in an amber bottle.

N-(5-(4-((1,1-Dioxidothiomorpholino)methyl)phenyl)-[1,2,4]triazolo[1,5-a]pyridin-2-yl)cyclopropanecarboxamide maleate Form I was also produced by dissolving N-(5-(4-((1,1-dioxidothiomorpholino)methyl)phenyl)-[1,2,4]triazolo[1,5-c]pyridin-2-yl)cyclopropanecarboxamide with about 1.1 mol. eq. maleic acid in acetonitrile/water at about 72° C. Next, a solution consisting of about 1.0 mol. eq. maleic acid dissolved in about 25 mL acetonitrile/water was charged. Then the reaction contents were cooled to about 65° C. and seeded with a small amount of N-(5-(4-((1,1-dioxidothiomorpholino)methyl)phenyl)-[1,2,4]triazolo[1,5-a]pyridin-2-yl)cyclopropanecarboxamide maleate Form I and held at the same temperature with agitation for about 4 hours. Afterwards, the reaction contents were cooled to about 0° C. at about 0.1° C./min. Next, the reaction contents were heat cycled twice. Each heat cycle consisted of heating the reaction content to about 50° C. at about 1° C./min, then cooling to about 0° C. at about 0.1° C./min. After the last cooling ramp, the reaction contents were held at about 0° C. with agitation for about 24 hours. Next, the reaction contents were filtered and washed with acetonitrile/water twice. The isolated solids were then dried in a vacuum oven at about 50° C. with $N_2$ purge.

N-(5-(4-((1,1-Dioxidothiomorpholino)methyl)phenyl)-[1,2,4]triazolo[1,5-a]pyridin-2-yl)cyclopropanecarboxamide maleate Form I was also produced by charging N-(5-(4-((1,1-dioxidothiomorpholino)methyl)phenyl)-[1,2,4]triazolo[1,5-a]pyridin-2-yl)cyclopropanecarboxamide, about 1 mol. eq. maleic acid, and THF in a reactor. The reaction contents were heated to about 55° C. Next, high purity water was charged into the reaction vessel. The reaction contents were then heated to about 65° C. Next, THF was charged into the reactor. The reaction contents were heated to about 63° C. and a clear solution was observed. Then a maleic acid solution (about 1.1 mol. eq. acid in water) was charged into the reaction vessel followed by water. The reaction contents were aged at about 65° C. for about 1 hour. Next, the reaction contents were cooled to about 45° C. and a small amount of N-(5-(4-((1,1-dioxidothiomorpholino)methyl)phenyl)-[1,2,4]triazolo[1,5-a]pyridin-2-yl)cyclopropanecarboxamide maleate Form I was added as a seed. The reaction contents were then cooled to about 5° over about 3 hours and aged overnight at about 5° C. The reaction contents were then filtered and washed with THF at about 5° C. The solids were then dried at about 50° C.

An X-ray powder diffraction (XRPD) pattern of filgotinib maleate Form I is shown in FIG. 1. The major peaks in the XRPD pattern are summarized in Table 1.

TABLE 1

Major Peaks in the XRPD Pattern for Filgotinib Maleate Form I

| No. | Pos. [°2Th.] | Rel. Int. [%] |
|---|---|---|
| 1 | 28.9 | 100.0 |
| 2 | 16.4 | 90.0 |
| 3 | 8.2 | 77.8 |
| 4 | 18.9 | 65.0 |
| 5 | 20.0 | 61.8 |
| 6 | 11.9 | 54.8 |
| 7 | 14.9 | 54.5 |
| 8 | 18.1 | 48.3 |
| 9 | 20.5 | 44.8 |
| 10 | 22.6 | 41.7 |

Filgotinib maleate Form I may be characterized by XRPD peaks at 8.2, 11.9, 16.4, and 18.9°2θ±0.2°2θ.

The differential scanning calorimetry (DSC) curve and thermogravimetric analysis (TGA) of filgotinib maleate Form I are shown in FIG. 2. The DSC curve is the top curve in the graph and the TGA curve is the bottom curve in the graph.

The proton nuclear magnetic resonance spectrum ($^1$H NMR) of filgotinib maleate Form I, which demonstrates that there is one molecule of maleic acid per molecule of filgotinib in filgotinib maleate Form I, is shown in shown in FIG. 3.

The XRPD pattern of filgotinib maleate Form I was collected with a PANalytical X'Pert PRO MPD diffractometer using the following experimental setting: 45 kV, 40 mA, Kα1=1.5406 Å, scan range 2-40°2θ, step size 0.0167°2θ, counting time: 15.875 s or 48.260 s. The DSC analysis was conducted on a TA Instruments Q2000 differential scanning calorimeter using approximately 2 to 3 mg of material, 10° C./min heating rate over a typical range of (−30° C.) to 300° C. or 20° C. to 350° C. The TGA data were obtained on a TA Instruments 2950 and Q5000 thermogravimetric analyzers using approximately 2 to 5 mg of material, 10° C./min heating rate over a typical range of 25 to 350° C.

Example 2

Pharmacokinetic Parameters after Oral Administration of Pharmaceutical Compositions Comprising Filgotinib Maleate Form I With and Without Fumaric Acid to Famotidine Pretreated Dogs The pharmacokinetic parameters of various formulations comprising filgotinib maleate Form I were tested in famotidine pretreated dogs in order to evaluate the effect of concurrent administration of acid reducing agents (ARAs). It was found that addition of fumaric acid to a pharmaceutical composition comprising filgotinib maleate Form I provided increased exposure of filgotinib in famotidine pretreated dogs compared to a control formulation that did not contain fumaric acid. Similar results were obtained with citric acid. Furthermore, the pharmaceutical composition comprising fumaric acid and filgotinib maleate Form I provided superior exposure of filgotinib in famotidine pretreated dogs relative to a formulation described in International Application Publication No. WO 2015/117980 (the "Reference Formulation"). The results are summarized in Table 2. A 100 mg dose of filgotinib was administered in each of the formulations.

TABLE 2

Pharmacokinetic Parameters after Oral Administration of Pharmaceutical Compositions Comprising Filgotinib Maleate Form I to Famotidine Pretreated Dogs

| Formulation | $AUC_{Last}$ of filgotinib (nM · hr) | $C_{max}$ of filgotinib (nM) | $T_{max}$ of filgotinib (hr) |
|---|---|---|---|
| With Fumaric Acid | 74600 (10400) | 9230 (2850) | 1.9 (2.1) |
| Without Fumaric Acid | 35100 (14500) | 5280 (2570) | 1.1 (0.7) |
| Reference Formulation | 48800 (16400) | 8400 (3900) | 1.2 (0.7) |

Mean values are reported with standard deviation included in parenthesis

Example 3

Pharmaceutical Composition Comprising Filgotinib Maleate Form I

A pharmaceutical composition comprising filgotinib maleate Form I and fumaric acid was developed for use in clinical trials in view of the data presented in Example 2. The components and amounts of the components in the pharmaceutical composition (the "Test Formulation") are described in Table 3.

TABLE 3

Pharmaceutical Composition Comprising Filgotinib Maleate Form I

| Component | Amount (weight %) |
|---|---|
| Filgotinib maleate Form I | 31.81 |
| Microcrystalline cellulose | 35.69 |
| Lactose monohydrate | 20.00 |
| Pregelatinized starch | 5.00 |
| Colloidal silicon dioxide | 1.00 |
| Magnesium stearate | 1.50 |
| Fumaric acid | 5.00 |

Example 4

Phase 1 Study

A Phase I, single center, open label, multiple cohort study was conducted with the Test Formulation to assess the relative bioavailability of the Test Formulation compared to the Reference Formulation in humans, as well as the effect of concurrent administration of acid-reducing agents (ARAs) on the pharmacokinetics of filgotinib in humans. The study designs are described below.

Relative Bioavailability

Following completion of screening, eligible subjects were randomized to a treatment sequence within a cohort. The treatments administered were as follows:

Treatment A: single 200 mg dose of filgotinib in Reference Formulation (2×100 mg tablets), administered in the AM, fasted Treatment B: single 200 mg dose of filgotinib in Test Formulation (1×200 mg tablet), administered in the AM, fasted Treatment C: single 100 mg dose of filgotinib in Reference Formulation (1×100 mg tablet), administered in the AM, fasted Treatment D: single 100 mg dose of filgotinib Test Formulation (1×100 mg tablet), administered in the AM, fasted

TABLE 4

Design of Relative Bioavailability Study

| Cohort | Day 1 | Days 2-9 | Day 10 |
|---|---|---|---|
| 1 (n = 26) | A | Washout | B |
|  | B | Washout | A |
| 2 (n = 26) | C | Washout | D |
|  | D | Washout | C |

Treatments A-D: Study treatments were administered in the morning following an overnight fast (no food or drinks except water, for at least 8 hours). Subjects continued to fast until after collection of the 4-hour PK sample, relative to study drug dosing. Additionally, subjects were restricted from water consumption 1 hour before until 2 hours after dosing, except for the 240 mL water given with the study treatment.

All study treatments were administered orally at the study center in the morning at approximately the same time on each day with 240 mL of still (non-carbonated) water.

Intensive PK sampling occurred relative to the morning dose of filgotinib at the following time points: Days 1 and 10: 0 (predose), 0.5, 1, 2, 3, 4, 6, 8, 12, 18, 24, 36, 48, 72, 96, and 120 hours postdose.

Plasma concentrations of filgotinib were determined using a validated LC-MS/MS method. Noncompartmental PK parameters of filgotinib were estimated using Phoenix WinNonlin® (Phoenix WinNonlin Professional, version 6.4; Pharsight Corporation, Mountain View, California) and summarized using descriptive statistics by treatment for each cohort. A parametric (normal theory) analysis of variance (ANOVA) using a mixed-effects model with treatment, period, and sequence as fixed effects and subject as a random effect were fitted to the natural logarithmic transformation of PK parameters ($AUC_{inf}$ and $C_{max}$) for filgotinib. The ratio of geometric least-squares means (GLSM) of the PK parameter in comparison between the Test Formulation versus the Reference Formulation and the two-sided 90% confidence interval (CI) for the ratio were calculated.

Filgotinib PK parameters and the associated statistical comparisons between the Test Formulation and the Reference Formulation are summarized in the following table. The data demonstrate that the Test Formulation and Reference Formulation resulted in comparable plasma exposures ($AUC_{inf}$ and $C_{max}$) of filgotinib at both 100 mg and 200 mg, with the 90% CIs of the GLSM ratios contained in the pre-specified comparable boundary of 70% to 143%. The 90% CIs for filgotinib ($AUC_{inf}$ and $C_{max}$ at 200 mg; $AUC_{inf}$ at 100 mg) were also within the bioequivalence bounds of 80% to 125%. $T_{max}$ and $t_{1/2}$ of filgotinib were also comparable for the Test Formulation and the Reference Formulation at both dose levels.

TABLE 5

Filgotinib Pharmacokinetic Parameters Following Single Doses of Test Formulation vs. Reference Formulation

| Filgotinib dose | PK Parameter | Test Mean (% CV) | Reference Mean (% CV) | Test vs. Reference % GLSM Ratio (90% CI) |
|---|---|---|---|---|
| 200 mg (n = 26) | $AUC_{inf}$ (µg · h/mL) | 5.31 (27.4) | 5.48 (27.5) | 97.4 (90.8, 104) |
|  | $C_{max}$ (µg/mL) | 1.78 (35.9) | 1.83 (45.1) | 101 (87.4, 118) |
|  | $T_{max}$ (h) [a] | 1.00 (0.50, 2.00) | 1.00 (1.00, 3.00) | — |
|  | $t_{1/2}$ (h) [a] | 7.50 (6.22, 9.34) | 6.88 (4.97, 9.08) | — |
| 100 mg (n = 26) | $AUC_{inf}$ (µg · h/mL) | 2.33 (25.0) | 2.31 (29.0) | 101 (94.8, 108) |
|  | $C_{max}$ (µg/mL) | 0.916 (35.8) | 0.852 (51.0) | 116 (98.3, 136) |
|  | $T_{max}$ (h) [a] | 1.00 (0.50, 1.00) | 1.00 (0.50, 2.00) | — |
|  | $t_{1/2}$ (h) [a] | 6.89 (4.60, 8.67) | 6.24 (4.50, 7.61) | — |

$AUC_{inf}$ = area under the plasma concentration versus time curve from 0 to infinity;
$C_{max}$ = maximum plasma concentration;
$T_{max}$ = time of $C_{max}$;
$t_{1/2}$ = terminal elimination half-life;
GLSM = geometric least-squares means;
CI = confidence interval;
[a] Median (Q1, Q3)

ARA Effect

Following completion of screening, eligible subjects were administered the following treatments:

Treatment M: single 200 mg dose of filgotinib in Test Formulation (1×200 mg tablet), administered in the AM, fasted Treatment N: famotidine 40 mg (1×40 mg tablet), administered twice daily, approximately 12 hours apart Treatment O: famotidine 40 mg (1×40 mg tablet), administered AM in a fasted state, followed by a single dose of filgotinib in Test Formulation (1×200 mg tablet), administered 2 hours after the AM dose of famotidine and an evening dose of famotidine 40 mg (1×40 mg tablet) administered approximately 12 hours after the AM dose of filgotinib

TABLE 6

Design of ARA Effect Study

| Cohort | Day 1 | Days 2-5 | Days 6-9 | Day 10 |
|---|---|---|---|---|
| 1 (n = 13) | M | Washout | N | O |

Treatment M: Filgotinib was administered following an overnight fast (no food or drinks except water, for at least 8 hours). Subjects continued to fast until after collection of the 4-hour PK sample, relative to study drug dosing. Additionally, subjects were restricted from water consumption 1 hour before until 2 hours after dosing, except for the 240 mL water given with the study treatment.

Treatment N: Famotidine was administered without regard to food.

Treatment O: The AM dose of famotidine was administered following an overnight fast (no food or drinks except water, for at least 8 hours), followed by a single dose of filgotinib administered 2 hours after the AM dose of famotidine. Subjects continued to fast until after collection of the 4-hour PK sample, relative to filgotinib dosing. Additionally, subjects were restricted from water consumption 1 hour before the AM dose of famotidine until 2 hours after filgotinib dosing, except for the 240 mL water given with the study treatments. The evening dose of famotidine was administered without regard to food.

All study treatments were administered orally at the study center in the morning at approximately the same time on each day with 240 mL of still (non-carbonated) water.

All meals and/or snacks given to subjects during their stay in the clinical study facility were standardized for all subjects and were similar in calorie and fat content and taken at approximately the same time each day (e.g., 07:30, 12:00, and 18:00). Components of meals (e.g., margarine, jelly, bread) were given to subjects in individual portions (e.g., 1 tablespoon) per the approved meal schedule. The provision of meal components in bulk (e.g., a jar of jelly for subjects to share) was not practiced.

Intensive PK sampling occurred relative to the morning dose of filgotinib at the following time points: Days 1 and 10: 0 (predose), 0.5, 1, 2, 3, 4, 6, 8, 12, 18, 24, 36, 48, 72, 96, and 120 hours postdose. The 120-hour PK sample following Day 1 filgotinib treatment was collected prior to study drug administration on Day 6.

Plasma filgotinib concentrations were determined using a validated LC-MS/MS method. Noncompartmental PK parameters of filgotinib were estimated using Phoenix WinNonlin® (Phoenix WinNonlin Professional, version 6.4; Pharsight Corporation, Mountain View, California) and summarized using descriptive statistics by treatment for each cohort. An ANOVA using a mixed-effects model with treatment as a fixed effect and subject as a random effect will be fitted to the natural logarithmic transformation of PK parameters ($AUC_{inf}$ and $C_{max}$) for filgotinib. The ratio of GLSM of the PK parameter in comparison between filgotinib dosed in combination with famotidine versus filgotinib dosed alone and the two-sided 90% CI for the ratio were calculated.

The effect of famotidine on filgotinib PK following administration of the Test Formulation is summarized in the following table. The data demonstrate that coadministration of famotidine with the Test Formulation (staggered by 2 hours) did not produce a clinically relevant effect on filgotinib PK.

TABLE 7

Effect of Famotidine on Filgotinib Pharmacokinetics When Administered with the Test Formulation.

| PK Parameter | 200-mg Filgotinib Test Formulation (N = 13) | 200-mg Filgotinib Test Formulation + Famotidine (N = 13) | % GLSM Ratio (90% CI) |
|---|---|---|---|
| $AUC_{inf}$ (μg · h/mL) | 4.61 (15.2) | 4.59 (23.3) | 98.0 (90.6, 106) |
| $C_{max}$ (μg/mL) | 1.54 (24.1) | 1.31 (29.4) | 82.5 (71.0, 95.8) |
| $T_{max}$ (h) | 1.00 (1.00, 2.00) | 2.00 (1.00, 2.00) | — |
| $t_{1/2}$ (h) | 7.42 (4.11, 8.94) | 8.18 (6.02, 9.81) | — |

$C_{max}$ and $AUC_{inf}$ presented as mean (% CV); $T_{max}$ and $t_{1/2}$ presented as Median (Q1, Q3)

The invention claimed is:

1. A pharmaceutical composition comprising . . . filgotinib maleate Form I characterized by an XRPD pattern substantially the same as shown in FIG. 1.

2. The pharmaceutical composition of claim 1, further comprising fumaric acid.

3. The pharmaceutical composition of claim 1 or 2, further comprising magnesium stearate.

4. The pharmaceutical composition of claim 1 or 2, further comprising magnesium stearate, microcrystalline cellulose, lactose monohydrate, pregelatinized starch, and colloidal silicon dioxide.

5. The pharmaceutical composition of claim 1 or 2, further comprising magnesium stearate, microcrystalline cellulose, lactose monohydrate, pregelatinized starch, colloidal silicon dioxide, PEG 3350, polyvinyl alcohol, talc, titanium dioxide, and iron oxide red.

6. A pharmaceutical composition according to claim 1 comprising:
   about 32 wt % filgotinib maleate Form I;
   about 36 wt % microcrystalline cellulose;
   about 20 wt % lactose monohydrate;
   about 5.0 wt % pregelatinized starch;
   about 1.0 wt % colloidal silicon dioxide;
   about 1.5 wt % magnesium stearate; and
   about 5.0 wt % fumaric acid.

7. A pharmaceutical composition according to claim 1 comprising:
   about 29 wt % to about 35 wt % filgotinib maleate Form I;
   about 32 wt % to about 40 wt % microcrystalline cellulose;
   about 18 wt % to about 22 wt % lactose monohydrate;
   about 4.5 wt % to about 5.5 wt % pregelatinized starch;
   about 0.9 wt % to about 1.1 wt % colloidal silicon dioxide;
   about 1.3 wt % to about 1.8 wt % magnesium stearate; and
   about 4.5 wt % to about 5.5 wt % fumaric acid.

8. The pharmaceutical composition of claim 1 or 2 wherein the composition is in the form of a tablet.

9. The pharmaceutical composition of claim 1 or 2 wherein the filgotinib maleate Form I is characterized by a differential scanning calorimetry (DSC) curve substantially the same as shown in FIG. 2.

10. The pharmaceutical composition of claim 1 or 2 wherein the filgotinib maleate Form I is characterized by thermogravimetric analysis (TGA) comprising a thermogram substantially the same as shown in FIG. 2.

11. The pharmaceutical composition of claim 1 or 2 wherein the filgotinib maleate Form I is characterized by a proton nuclear magnetic resonance spectrum ($^1$H NMR) substantially the same as shown in FIG. 3.

12. A method of treating an inflammatory disease or disorder . . . according to claim 1 or 2 to a patient in need thereof, wherein the inflammatory disease or disorder is selected from the group consisting of rheumatoid arthritis, Crohn's disease, ulcerative colitis, alopecia areata, uveitis, acute graft-versus-host disease, cutaneous lupus nephritis, membranous lupus nephritis, atopic dermatitis, psoriasis, ankylosing spondylitis and psoriatic arthritis.

* * * * *

UNITED STATES PATENT AND TRADEMARK OFFICE
CERTIFICATE OF CORRECTION

| | | |
|---|---|---|
| PATENT NO. | : 11,975,008 B2 | |
| APPLICATION NO. | : 17/186446 | |
| DATED | : May 7, 2024 | |
| INVENTOR(S) | : David Alonzo, Bei Li and Dimitrios Stefanidis | |

It is certified that error appears in the above-identified patent and that said Letters Patent is hereby corrected as shown below:

On the Title Page

Item (73) please delete "(73) Assignee: Galapagos NV, Mechelen, Belgium" Please correct the Assignee to appear as follows:
-- (73) Assignee: Alfasigma S.p.A., Bologna, (IT) --.

In the Claims

Column 11, Line 36, cancel the text beginning with "1. A pharmaceutical composition" to and ending "as shown in Fig. 1." in Line 38, and insert the following claim:
-- 1. A pharmaceutical composition comprising a therapeutically effective amount of filgotinib maleate Form I characterized by an XRPD pattern substantially the same as shown in Fig. 1. --.

Signed and Sealed this
Twelfth Day of November, 2024

*Katherine Kelly Vidal*

Katherine Kelly Vidal
*Director of the United States Patent and Trademark Office*